(12) United States Patent
Spangler et al.

(10) Patent No.: US 6,278,015 B1
(45) Date of Patent: Aug. 21, 2001

(54) PROCESS FOR TRIFLUOROACETATE ESTERS AND THIOESTERS

(75) Inventors: Lori Ann Spangler, Churchville; Fereydon Abdesaken, Dresher; Joshua Anthony Chong, Lansdale, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/617,381

(22) Filed: Jul. 17, 2000

Related U.S. Application Data

(60) Provisional application No. 60/144,803, filed on Jul. 21, 1999.

(51) Int. Cl.[7] .................................................. C07C 69/63
(52) U.S. Cl. ..................... 560/227; 560/265; 560/239; 560/226; 560/228; 560/203
(58) Field of Search ...................................... 560/227, 255

(56) References Cited

U.S. PATENT DOCUMENTS

| | | | | |
|---|---|---|---|---|
| 2,012,812 | * | 8/1935 | Guinot et al. ......................... | 560/265 |
| 4,701,551 | * | 10/1987 | DesBois et al. ..................... | 560/226 |
| 4,730,082 | * | 3/1988 | Amiet et al. .......................... | 560/227 |
| 4,879,407 | * | 11/1989 | Amiet et al. .......................... | 560/227 |
| 4,916,256 | * | 4/1990 | Grego et al. .......................... | 560/227 |
| 5,405,991 | | 4/1995 | Feist et al. ............................ | 560/239 |

FOREIGN PATENT DOCUMENTS

WO 96/26185   8/1996   (WO) .

* cited by examiner

*Primary Examiner*—Gary Geist
*Assistant Examiner*—Hector M. Reyes
(74) *Attorney, Agent, or Firm*—Clark R. Carpenter

(57) ABSTRACT

The present invention provides a process for preparing esters or thioesters of trifluoroacetic acid from trifluoroacetyl chloride and an alcohol or a thiol with the ester or thioester being present as the solvent. Esters and thioesters of trifluoroacetic acid are fine chemical intermediates which can be used in the manufacture of pharmaceuticals, agricultural chemicals, liquid crystals, dyes and industrial chemicals. Trifluoroacetate esters and thioesters can also be used as solvents in the manufacture of other fine chemicals, pharmaceuticals, agricultural chemicals, liquid crystals, industrial chemicals and dyes.

10 Claims, No Drawings

PROCESS FOR TRIFLUOROACETATE ESTERS AND THIOESTERS

This application claims benefit of provisional application 60/144,803, filed Jul. 21, 1999.

The present invention relates to a process for preparing esters or thioesters of trifluoroacetic acid from trifluoroacetyl chloride and an alcohol or a thiol. Esters or thioesters of trifluoroacetic acid are fine chemical intermediates which can be used in the manufacture of pharmaceuticals, agricultural chemicals, liquid crystals, dyes and industrial chemicals. Trifluoroacetate esters can also be used as solvents in the manufacture of other fine chemicals, pharmaceuticals, agricultural chemicals, liquid crystals, dyes and industrial chemicals.

There are several processes previously disclosed which can be used to produce trifluoroacetate esters. U.S. Pat. No. 4,916,256 teaches vapor phase reactions which must employ a substantial stoichiometric excess of the toxic and relatively expensive trifluoroacetyl chloride to react with an alcohol to produce a trifluoroacetate ester. U.S. Pat. No. 5,405,991 teaches the reaction of an acid chloride with an alcohol to form a trifluoroacetate ester but with the necessity of having a catalyst present which is an alkali metal salt or an onium salt of the carboxylic acid corresponding to the acid chloride starting material. U.S. Pat. No. 4,701,551 discloses reaction of trifluoroacetic acid with an alcohol to form trifluoroacetate esters but liquid HF is required as a catalyst. U.S. Pat. No. 4,730,082 discloses a multi-step process to produce methyl trifluoroacetate from trifluoroacetic acid and methanol; a catalytic amount of a strong acid is required in one of the steps. WO 96/26185 A1 discloses formation of thioesters by reacting trifluoroacetic anhydride with thiols in the presence of pyridine and 4-dimethylaminopyridine (DMAP). None of these references, either individually or collectively, teach or suggest the process of the present invention.

We have found in the process of the present invention that the product trifluoroacetate ester or thioester itself is an excellent solvent for the reaction. The reaction is run at relatively low temperature, from about ambient to somewhat below the boiling point of trifluoroacetyl chloride. No other catalyst or reagent is required. Hydrogen chloride, which is a by-product of the reaction, is removed at the end of the reaction by warming the reaction mixture to room temperature with stirring. The ester or thioester product obtained by this process is of already high purity, but purity can be increased to >99% by distillation. The resultant advantages of the process of the present invention include:

(i) an ease of purification of the desired ester or thioester product since no other solvent is present which must be removed using distillation or other techniques, (ii) the solubility of trifluoroacetyl chloride in the desired ester or thioester is high which leads to concentrated reaction mixtures and more pounds of product ester or thioester per reactor, (iii) the high solubility of trifluoroacetyl chloride in the desired ester or thioester results in a safer process since the process control of the toxic trifluoroacetyl chloride to prevent it from boiling away (b.p. is −27° C.) is not just dependent on the reactor cooling, and (iv) no other reagents or catalysts are required for the desired ester or thioester formation.

Accordingly, this invention provides a process for the preparation of a trifluoroacetate compound of formula (I) from trifluoroacetyl chloride and a compound of formula (II)

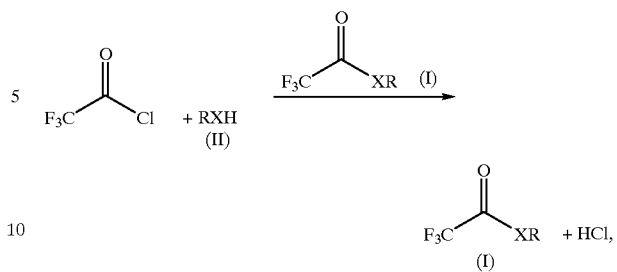

wherein
R is alkyl or alkyl substituted with alkoxy or haloalkoxy, and
X is an oxygen or a sulfur atom which comprises the steps of
(i) reacting trifluoroacetyl chloride with a compound of formula (II) in the initial presence of an amount of said trifluoroacetate compound of formula (I) at a temperature of 20° C. or less to produce the trifluoroacetate compound of formula (I) and
(ii) degassing the mixture at ambient temperature to remove the HCl by-product and any residual trifluoroacetyl chloride.

As used herein, the term "alkyl" refers to straight and branched aliphatic hydrocarbon chains, for example, methyl, ethyl, n-propyl, isopropyl, it-butyl, sec-butyl, tert-butyl, isoamyl and n-hexyl. When the alkyl group possesses an asymmetric carbon atom, the term alkyl is meant to include either enantiomeric form or a mixture thereof The term "alkoxy" refers to a straight or a branched aliphatic hydrocarbon chain attached to an oxygen atom, for example, methoxy, ethoxy, isopropoxy, n-butoxy and the like. The term "haloalkoxy" refers to an alkoxy group substituted with one or more halo groups, for example, chloromethoxy, chlorodifluoromethoxy, trifluoromethoxy, perfluoroethoxy, 2-bromoethoxy and the like. The term "halo" refers to a fluorine, chlorine or a bromine atom.

In a preferred process of this invention, R is $(C_1–C_6)$alkyl or $(C_1–C_6)$alkyl substituted with $(C_1–C_4)$alkoxy.

In a more preferred process of this invention, R is $(C_1–C_4)$alkyl.

In an even more preferred process of this invention, R is methyl, ethyl or isopropyl.

In the most preferred process of this invention, R is ethyl.

More specifically, the process for the preparation of esters or thioesters of trifluoroacetic acid of this invention involves reacting trifluoroacetyl chloride with an alcohol or a thiol at a low temperature in the presence of the desired product of formula (I) as a solvent in a first step and, at the end of the desired reaction, degassing the mixture at room temperature to remove hydrogen chloride by-product and any residual trifluoroacetyl chloride. These gasses are treated, usually by passing them through a scrubber or, in the case of trifluoroacetyl chloride, the gasses can be recycled, for example, by either capturing in a scrubber filled with the ester or thioester of trifluoroacetic acid which will be used as solvent in the subsequent reaction or by condensation. The ester or thioester of trifluoroacetic acid produced in this reaction is already of high purity, but the purity can be increased to >99% by distillation.

The alcohol (ROH) or thiol (RSH) can be selected from alcohols or thiols having from 1 to 6 carbon atoms. The alkyl groups R can be straight chain or branched chain. The R group can be substituted with alkoxy groups and with haloalkoxy groups.

The reaction step (i) is carried out at a temperature which is near the boiling point of trifluoroacetyl chloride. Typical reaction temperatures range from about −40° C. to about 20° C., preferably from about −30° C. to about 0° C., and more preferably from about −25° C. to about −15° C.

The process is performed as follows: the dry reactor is charged with a heel (recycled material, most usually from the previous reaction batch) of the desired product ester or thioester and cooled to the low temperature. The first reagent, which can be either trifluoroacetyl chloride or the compound of formula (II), is added. The second reagent is added at a rate to keep the internal temperature of the reactor at the desired temperature. After reaction is complete, the mixture is warmed to room temperature to degas and remove the hydrogen chloride and any residual trifluoroacetyl chloride. The reactor now contains the desired ester or thioester of trifluoroacetic acid. The purity can be raised further by distillation at atmospheric pressure, or under reduced pressure.

The addition order is variable. Preferably, the trifluoroacetyl chloride is dissolved in the heel of trifluoroacetate ester or thioester and then treated with the alcohol or thiol as appropriate. However, the reaction can also be performed by dissolving the alcohol or thiol into the heel of trifluoroacetate ester or thioester and then adding trifluoroacetyl chloride to that mixture.

The charges of trifluoroacetyl chloride and a compound of formula (II) are usually made in a molar ratio near to 1:1. Either reagent can be used in a slight excess, depending on costs and convenience. Thus, the molar ratio of compound of formula (II) to trifluoroacetyl chloride is conveniently in the range of 1.10 to 0.90, preferably in the range of 1.05 to 0.98. For example, the compound of formula (II) can be used in excess at a molar ratio of 1.01 to 1.10. More desirable is the usage of a smaller excess of the compound of formula (II) at a molar ratio of 1.01 to 1.02 as the residual compound of formula (II) can easily be removed during distillation when it is used in a smaller excess. Alternatively, trifluoroacetyl chloride can be used in a slight excess (i.e., the molar ratio of the compound of formula (II) to trifluoroacetyl chloride is 0.99 to 0.90) and removed from the product ester or thioester during the degassing. If the higher excess is used, the excess trifluoroacetyl chloride can either be recycled by condensation and returned to the next batch, or captured in a scrubber charged with the trifluoroacetate ester or thioester to be used as the heel in a subsequent batch.

The molar ratio of the desired trifluoroacetate ester or thioester used as solvent to the amount of trifluoroacetyl chloride can vary over quite wide limits. A molar ratio of from about 0.5 to about 2 is a preferred range.

The process is generally run as a batch reaction, but could be run as a continuous process. It is also possible to run the reaction under a slight pressure of trifluoroacetyl chloride, preferably not higher than 50 psig. Reaction under pressure can be performed at the higher end of the described temperature range without losing reagents and products to the scrubber.

Although other solvents such as aromatics, for example toluene, or ethers, esters, or alkanes can be used for this process in place of the desired trifluoroacetate ester or thioester, the solubility of trifluoroacetyl chloride in these solvents at the reaction temperatures tends to be lower, leading to decreased productivity. Additionally, the solvents must then be separated from the product ester or thioester in order to yield high-purity product.

The following examples and experimental procedures are provided for additional guidance to the practitioner.

EXAMPLE 1
Preparation of Ethyl Trifluoroacetate

A heel of 187 g of ethyl trifluoroacetate was cooled to −19° C. To this was added 199 g of trifluoroacetyl chloride, and the mixture was maintained at −190 to −25° C. To this was added 55.8 g of ethanol over 60 min, followed by an additional 14 g of ethanol over 45 min. The mixture was then allowed to warm to room temperature with stirring and using a scrubber filled with 10% aqueous sodium hydroxide. The resulting 396 g of ethyl trifluoroacetate was transferred to a still and distilled at atmospheric pressure to yield 360 g of ethyl trifluoroacetate, >99% pure.

EXAMPLE 2
Preparation of Ethyl Trifluoroacetate

A heel of 237 g of ethyl trifluoroacetate was cooled to −19° C. To this was added 132.5 g of trifluoroacetyl chloride, and the mixture was maintained at −19° C. to −25° C. To this was added 37 g of ethanol over 60 min, followed by an additional 9.5 g of ethanol over 45 min. The mixture was then allowed to warm to room temperature with stirring and using a scrubber filled with 10% aqueous sodium hydroxide. The resulting ethyl trifluoroacetate was transferred to a still and distilled at atmospheric pressure to yield 128 g of ethyl trifluoroacetate, >99% pure.

EXAMPLE 3
Preparation of Isopropyl Trifluoroacetate

A heel of 180 g of isopropyl trifluoroacetate was cooled to −19° C. To this was added 132.5 g of trifluoroacetyl chloride, and the mixture was maintained at −19° C. to −25° C. To this was added 48.6 g of isopropanol over 60 min, followed by an additional 12.1 g of isopropanol over 45 min. The mixture was then allowed to warm to room temperature with stirring and using a scrubber filled with 10% aqueous sodium hydroxide. The resulting isopropyl trifluoroacetate weighed 282.6 g, and was of >97% purity.

EXAMPLE 4
Preparation of Ethyl Trifluoroacetate

A heel of 237 g of ethyl trifluoroacetate is cooled to −30° C. To this is added 132.5 g of trifluoroacetyl chloride, and the mixture maintained at −30° C. To this is added 37 g of ethanol over 60 min, followed by an additional 9.5 g of ethanol over 45 min. The mixture is then allowed to warm to room temperature with stirring and a scrubber filled with 10% aqueous sodium hydroxide. The resulting 379 g of ethyl trifluoroacetate is transferred to a still and is distilled at atmospheric pressure to yield 360 g of ethyl trifluoroacetate, >99% pure.

EXAMPLE 5
Preparation of Methyl Trifluoroacetate

A heel of 128 g of methyl trifluoroacetate is cooled to −20° C. To this is added 132.5 g of trifluoroacetyl chloride, and the mixture is maintained at −20° C. To this is added 25.9 g methanol over 60 min, followed by an additional 6.4 g of methanol over 45 min. The mixture is then allowed to warm to room temperature with stirring and using a scrubber filled with 10% aqueous sodium hydroxide. The resulting 256 g of methyl trifluoroacetate is transferred to a still and is distilled at atmospheric pressure to yield 243 g of methyl trifluoroacetate, >99% pure.

EXAMPLE 6
Preparation of Ethyl Trifluoroacetate

A reactor is set up so the first scrubber contains 100 g of ethyl trifluoroacetate, and a second scrubber contains 10% aqueous sodium hydroxide. A heel of 187 g of ethyl trifluoroacetate is cooled in the reactor to −10° C. To this is added 199 g of trifluoroacetyl chloride, and the mixture is maintained at −10° C. To this is added 55.8 g of ethanol over 60 min, followed by an additional 14 g of ethanol over 45 min. The mixture is then allowed to warm to room temperature with stirring. The resulting 356 g of ethyl trifluoroacetate is transferred to a still and is distilled at atmospheric pressure to yield 338 g of ethyl trifluoroacetate, >99% pure. The ethyl trifluoroacetate from the first scrubber, which now contains some trifluoroacetyl chloride, is used as the heel for the next reaction.

EXAMPLE 7

Preparation of S-ethyl Trifluorothioacetate

A heel of 158 g of S-ethyl trifluorothioacetate is cooled to −25° C. To this is added 199 g of trifluoroacetyl chloride, and the mixture is maintained at −25° C. To this is added 75.1 g of ethanethiol over 60 min, followed by an additional 18.8 g of ethanethiol over 45 min. The mixture is then allowed to warm to room temperature with stirring and using a scrubber filled with 10% aqueous sodium hydroxide. The resulting 391 g of S-ethyl trifluorothioacetate is transferred to a still and is distilled at atmospheric pressure to yield 375 g of S-ethyl trifluorothioacetate, >99% pure.

We claim:

1. A process for the preparation of a trifluoroacetate compound of formula (I) from trifluoroacetyl chloride and a compound of formula (II)

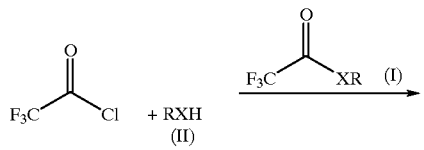

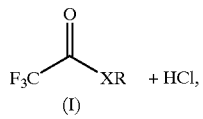 + HCl, wherein

R is alkyl or alkyl substituted with alkoxy or haloalkoxy, and

X is an oxygen or a sulfur atom which consists of the steps of
  (i) reacting trifluoroacetyl chloride with a compound of formula (II) in the initial presence of an amount of said trifluoroacetate compound of formula (I) at a temperature of 20° C. or loss to produce the trifluoroacetate compound of formula (I) and
  (ii) degassing the mixture at ambient temperature to remove the HCl by-product and any residual trifluoroacetyl chloride.

2. The process of claim 1 wherein R is $(C_1-C_6)$alkyl or $(C_1-C_6)$alkyl substituted with $(C_1-C_4)$alkoxy.

3. The process of claim 2 wherein R is $(C_1-C_4)$alkyl.

4. The process of claim 3 wherein R is methyl, ethyl or isopropyl.

5. The process of claim 4 wherein R is ethyl.

6. The process as in any one of the preceding claims wherein the molar ratio of the compound of formula (II) to the trifluoroacetyl chloride in step (i) is from 1.10 to 0.90.

7. The process of claim 6 wherein the molar ratio is from 1.05 to 0.98.

8. The process of claim 7 wherein the molar ratio is from 1.02 to 1.01.

9. The process of claim 6 wherein the molar ratio of the said trifluoroacetate compound of formula (I) initially present in step (i) to the trifluoroacetyl chloride is from 0.5 to 2.

10. The process of claim 6 wherein step (i) is carried out at a temperature of −30° C. to 0° C.

* * * * *